US009347926B2

(12) United States Patent
Silvis et al.

(10) Patent No.: US 9,347,926 B2
(45) Date of Patent: May 24, 2016

(54) EXHAUST SAMPLING SYSTEM AND METHOD FOR SYNCHRONIZING TIME ALIGNMENT AND DILATION

(71) Applicant: AVL TEST SYSTEMS, INC., Plymouth, MI (US)

(72) Inventors: William Martin Silvis, Ann Arbor, MI (US); Sarah Montgomery Kingham, Dexter, MI (US)

(73) Assignee: AVL TEST SYSTEMS, INC., Plymouth, MI (US)

( * ) Notice: Subject to any disclaimer, the term of this patent is extended or adjusted under 35 U.S.C. 154(b) by 0 days.

(21) Appl. No.: 14/406,624

(22) PCT Filed: Jun. 11, 2013

(86) PCT No.: PCT/US2013/045094
§ 371 (c)(1),
(2) Date: Dec. 9, 2014

(87) PCT Pub. No.: WO2013/188346
PCT Pub. Date: Dec. 19, 2013

(65) Prior Publication Data
US 2015/0177203 A1   Jun. 25, 2015

Related U.S. Application Data

(60) Provisional application No. 61/658,050, filed on Jun. 11, 2012.

(51) Int. Cl.
*G01M 15/10* (2006.01)
*G01N 1/22* (2006.01)
(Continued)

(52) U.S. Cl.
CPC ............ *G01N 33/0006* (2013.01); *F01N 11/00* (2013.01); *F02D 41/1444* (2013.01);
(Continued)

(58) Field of Classification Search
CPC .... F01N 11/00; F01N 2560/00; G01M 15/10; G01M 15/102; G01N 1/2252
USPC .......................................................... 702/89
See application file for complete search history.

(56) References Cited

U.S. PATENT DOCUMENTS 6,256,576 B1    7/2001   Wild et al.
6,470,732 B1 * 10/2002  Breton ................. F01N 13/008
                                                    73/114.69
(Continued)

FOREIGN PATENT DOCUMENTS

CN          1849446 A      10/2006
CN          1945254 A       4/2007
WO     WO-2012018344 A1    2/2012

OTHER PUBLICATIONS

International Search Report and Written Opinion of the International Searching Authority for PCT/US2013/045094, mailed Sep. 4, 2013; ISA/KR.

(Continued)

*Primary Examiner* — Michael Nghiem
*Assistant Examiner* — Peter Ngo
(74) *Attorney, Agent, or Firm* — Harness, Dickey & Pierce, P.L.C.

(57) ABSTRACT

A system and method is provided for synchronizing a first and second signal of an exhaust sampling system. The first signal is generated by a first instrument and includes an exhaust flow rate component and a first instrument time stamp component. The second signal is generated by a second instrument and includes a pollutant concentration component and a second instrument time stamp component. The second instrument also generates a tertiary signal that has been influenced by the first signal and includes a second instrument time stamp component. A synchronization module determines a time relationship for synchronizing the first signal and the second signal by comparing the first flow rate component and the first instrument time stamp component of the first signal to the tertiary signal and the second instrument time stamp component of the tertiary signal. The synchronization provides accurate calculation of a pollutant mass flow rate.

25 Claims, 4 Drawing Sheets (51) Int. Cl.
*G01N 33/00* (2006.01)
*F01N 11/00* (2006.01)
*F02D 41/14* (2006.01)
*F02D 41/28* (2006.01)

(52) U.S. Cl.
CPC ............ *F02D41/1445* (2013.01); *F02D 41/28* (2013.01); *G01M 15/10* (2013.01); *G01M 15/102* (2013.01); *G01N 1/22* (2013.01); *G01N 1/2252* (2013.01); *F01N 2560/00* (2013.01); *F02D 41/1466* (2013.01); *F02D 41/1467* (2013.01); *F02D 2041/288* (2013.01); *F02D 2250/14* (2013.01); *Y02T 10/47* (2013.01)

(56) References Cited

U.S. PATENT DOCUMENTS

| | | | |
|---|---|---|---|
| 7,974,210 B2 * | 7/2011 | Sugita | F02D 41/266 370/252 |
| 2003/0131586 A1 | 7/2003 | Kato et al. | |
| 2011/0213540 A1 | 9/2011 | Tripathi et al. | |
| 2012/0109495 A1 | 5/2012 | Tripathi et al. | |

OTHER PUBLICATIONS

Chinese Office Action for Application No. 201380030826.6 dated Jan. 18, 2016.

* cited by examiner

EXHAUST SAMPLING SYSTEM AND METHOD FOR SYNCHRONIZING TIME ALIGNMENT AND DILATION

CROSS-REFERENCE TO RELATED APPLICATIONS

This application claims the benefit of U.S. Provisional Application No. 61/658,050, filed on Jun. 11, 2012, the entirety of which is incorporated herein by reference.

FIELD

The present disclosure relates to an exhaust sampling system and method that synchronizes the time alignment and time sampling rates of multiple data-carrying signals.

BACKGROUND

Emissions control of internal combustion engines has become a priority in recent years and emissions control regulations continue to set more stringent standards for the emissions produced by modern-day engines. More particularly, these regulations often target emissions contained in the exhaust produced by internal combustion engines including carbon monoxide, carbon dioxide, NOx, unburned hydrocarbons and particulate matter, which is mostly soot. As such, manufacturers of compression ignition engines and spark ignition engines alike have developed various emissions control devices. Such emissions control devices include exhaust oxidation catalysts that remove carbon monoxide, hydrocarbon, and NOx emissions and exhaust particulate filters that remove particulate matter.

In testing engines for emissions compliance, it is desirable to determine the mass of pollutant in the exhaust produced by the engine. However, accurate calculation of the pollutant mass is problematic when the time of measurement of a pollutant concentration and an exhaust flow rate are not properly synchronized.

Multiple instruments are used to measure the necessary parameters for calculating the pollutant mass including, for example, exhaust flow rate and soot concentration. The multiple instruments generate signals that are not easily synchronized in time because the signals generated by the instruments may be captured by different recorders and/or may not start out aligned in time. Furthermore, there may be a gain or loss of time between the signals when measured over a testing interval if the clock rates are slightly different. Without first synchronizing the signals that carry the exhaust flow rate and pollutant concentration data, it is not possible to accurately calculate the pollutant mass. What is needed is a system and method for synchronizing these signals in time at the beginning of the testing interval and all points occurring along the testing interval such that accurate pollutant mass values can be calculated.

SUMMARY

Generally, the subject disclosure provides for an exhaust sampling system and method for synchronizing the time alignment and sampling rate of multiple data-carrying signals.

In one form, a system for sampling exhaust produced by an engine is provided. The system includes a first instrument that measures a first flow rate of the exhaust passing by the first instrument. In response to measuring the first flow rate, the first instrument generates a first signal. The first signal includes a first flow rate component and a first instrument time stamp component. The first flow rate component indicates the first flow rate that is measured by the first instrument. The first instrument time stamp component is associated with sampling the exhaust at a first time. More particularly, the first flow rate measured by the first instrument may be an exhaust flow rate of the exhaust leaving the engine. As such, the first flow rate component of the first signal may be more particularly defined as an exhaust flow rate component.

The system also includes a second instrument. The second instrument measures a pollutant concentration of the exhaust passing by the second instrument. In response to measuring the pollutant concentration of the exhaust, the second instrument generates a second signal. The second signal includes a pollutant concentration component and a second instrument time stamp component. The pollutant concentration component indicates the pollutant concentration that is measured by the second instrument. The second instrument time stamp component is associated with sampling the exhaust at the first time.

While measuring the pollutant concentration, the second instrument generates a tertiary signal. The tertiary signal includes a second instrument time stamp component such that the second instrument time stamp component is shared by the second signal and the tertiary signal. The tertiary signal indicates a signal that has a component that is influenced by the flow rate measured by the first instrument. More particularly, the tertiary signal measured by the second instrument may be a filter flow rate of the sample flowing proximate to an exhaust particulate filter. As such, the flow rate component of the tertiary signal may be more particularly defined as a filter flow rate component and it is influenced by the first variable measured by the first instrument. It may also be a pressure measurement of a pressure internal to the instrument used for determining a filter flow, or another pressure used for purposes of monitoring or doing corrections of measured signals.

The system further includes a synchronization module. The synchronization module receives and processes the first signal, the second signal, and the tertiary signal to determine a time relationship between the first signal and the second signal. The synchronization module determines the time relationship between the first signal and the second signal by comparing the first flow rate component and the first instrument time stamp component of the first signal to the second instrument tertiary signal and the second instrument time stamp component of the tertiary signal. By determining this time relationship, synchronization of the first signal and the second signal is possible.

In another form, a method of synchronizing signals of an exhaust sampling system is provided. The method includes the step of detecting a first signal from a first instrument. The first signal includes an exhaust flow rate component indicating an exhaust flow rate from an engine. The first signal also includes a first instrument time stamp component associated with sampling the exhaust at a first time. The method also includes the step of detecting a second signal from a second instrument. The second signal includes a pollutant concentration component indicating the pollutant concentration of exhaust passing by the second instrument. The second signal also includes a second instrument time stamp component associated with sampling the exhaust at the first time.

The method further provides the step of detecting a tertiary signal from the second instrument. The tertiary signal includes a filter flow rate component indicating the flow rate of sample gas in the second instrument, whereby the tertiary signal exhibits an influence from the first signal of the first instrument. The tertiary signal may alternatively include a pressure measurement exhibiting an influence for the first signal of the first instrument. The tertiary signal also includes the second instrument time stamp component.

In response to detecting the first signal, the second signal, and the tertiary signal, the method proceeds to the step of determining a time relationship between the first signal and the second signal. The influence of the first signal on the tertiary signal is detected and compared to the first signal. Advantageously, the time relationship may be used to align the first signal and the second signal in time, allowing for accurate calculation of the pollutant mass of the exhaust.

Further areas of applicability will become apparent from the description provided herein. The description and specific examples in this summary are intended for purposes of illustration only and are not intended to limit the scope of the present disclosure.

DRAWINGS

The features and advantages described above and other features and advantages of the present disclosure will be readily appreciated, as the same becomes better understood by reference to the following detailed description when considered in connection with the accompanying drawings. These drawings are for illustrative purposes of only select embodiments and not all possible implementations and are not intended to limit the scope of the present disclosure, wherein.

DETAILED DESCRIPTION

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Figure 1:
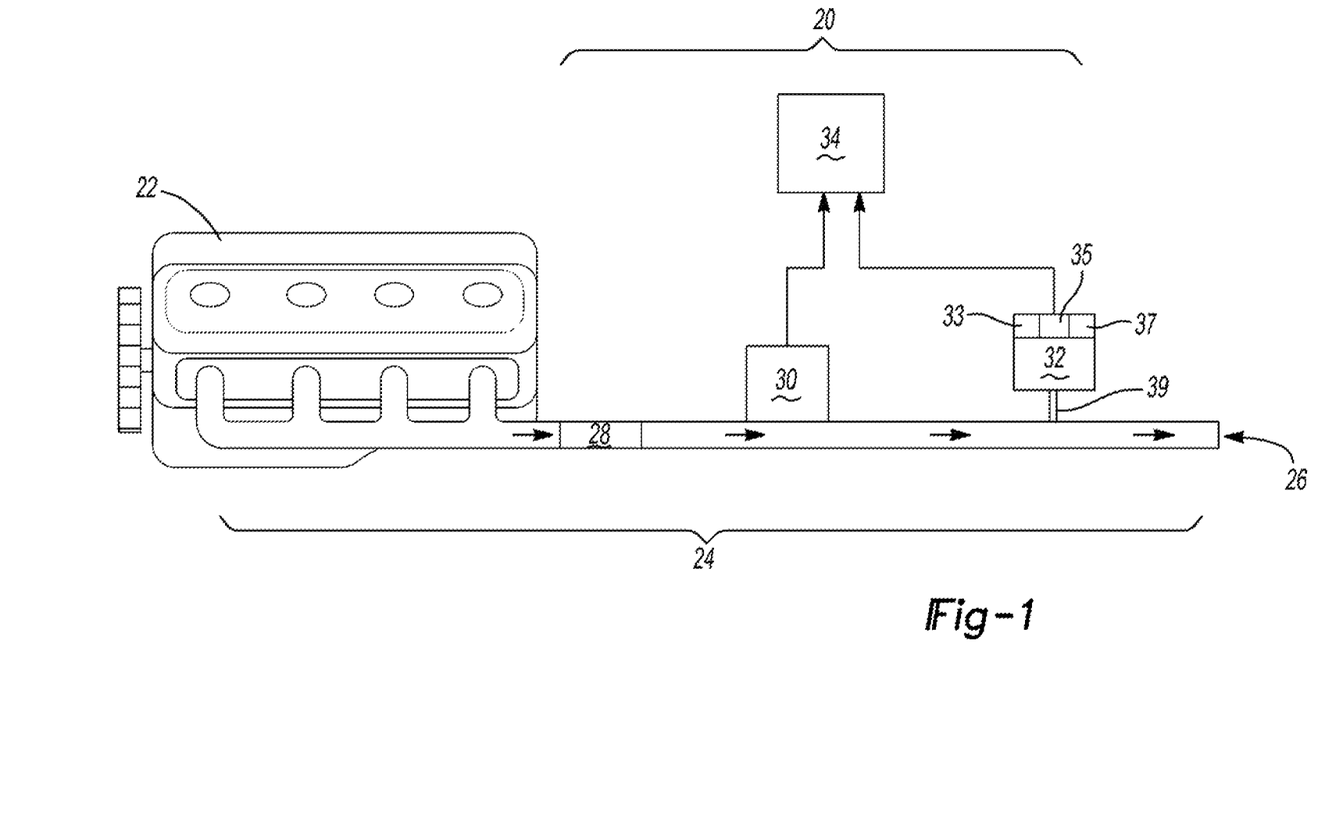
FIG. 1 is a schematic diagram illustrating an exemplary exhaust sampling system constructed in accordance with the subject disclosure.

Referring to FIG. 1, a system 20 for measuring pollutant mass in exhaust produced by an engine 22 is disclosed. The system 20 generally samples exhaust as it passes through an exhaust path 24 including one or more pipes that lead away from the engine 22. It should be appreciated that the exhaust travels through the exhaust path 24 in a flow direction that generally moves away from the engine 22 and towards an outlet 26 of the exhaust path 24. The system and method disclosed herein applies equally to compression ignition engines such as diesel engines and to spark ignition engines such as gasoline engines. Accordingly, various emissions control devices may be disposed along the exhaust path 24. For example, an exhaust particulate filter 28 may be disposed along the exhaust path 24 downstream of the engine 22 with respect to the flow direction of the exhaust. The exhaust particulate filter 28 generally removes particulate matter, also referred to as soot, from the exhaust passing through the exhaust path 24. It should be appreciated that the exhaust particulate filter 28 may be a diesel particulate filter (DPF) when included in the exhaust path 24 of a compression ignition engine.

The system 20 disclosed includes a first instrument 30 and a second instrument 32 disposed along the exhaust path 24 that leads away from the engine 22. The first instrument 30 may be positioned along the exhaust path 24 proximate to the engine 22 for sampling the exhaust exiting the engine 22. As such, the first instrument 30 may be a standalone sensor or part of an engine-management system. The first instrument 30 measures a first flow rate of the exhaust passing by the first instrument 30. More particularly, the first flow rate may be an exhaust flow rate of the exhaust leaving the engine 22.

The first instrument 30 generates a first signal in response to measuring the exhaust flow rate. The first signal that is generated by the first instrument 30 includes a first flow rate component indicating the first flow rate. Accordingly, the first flow rate component may be an exhaust flow rate component that indicates the exhaust flow rate of the exhaust leaving the engine 22. The first signal may also include a first instrument time stamp component that is associated with sampling the exhaust at a first time. The first instrument time stamp component may be generated by a clock associated with the first instrument 30.

The second instrument 32 may be spaced from the first instrument 30 such that the second instrument 32 is positioned downstream of the first instrument 30 with respect to the flow direction of the exhaust. While the second instrument 32 is described and shown as being located downstream of the first instrument 30, the relative position of the first instrument 30 and the second instrument 32 is not limited as such. It may also be upstream of the first instrument 30.

The second instrument 32 may be positioned along the exhaust path 24 and may be an emission measurement system for the determination of real-time soot or particulate matter emissions, or gaseous pollutant emissions within exhaust gas of the engine 22. In one configuration, the second instrument 32 is an AVL PM PEMS manufactured and produced by AVL of Graz, Austria. Accordingly, the second instrument 32 may include a micro-soot sensor 33, a filter 35, and a flow meter 37, each schematically represented in FIG. 1 as being associated with the second instrument 32.

In operation, the second instrument 32 receives an exhaust sample from the exhaust path 24 via a tube 39 that is in fluid communication with the exhaust flow disposed within the exhaust path 24. The second instrument 32 measures a soot concentration or a gaseous pollutant concentration and a flow rate or pressure within the instrument 32. The second instrument 32 generates a second signal in response to measuring the pollutant concentration and the second flow rate. While the second signal is described as being generated in response to the second flow rate, the second signal could be generated in response to virtually any parameter that correlates with the exhaust flow disposed within the exhaust path 24. For example, the second signal could be generated in response to pressure within the second instrument 32, which is influenced by the first flow rate (i.e., the exhaust flow in the exhaust path 24). The pressure within the second instrument 32 may be used to generate the second signal, as the pressure within the second instrument 32 changes virtually instantaneously with changes in pressure within the exhaust path 24.

Regardless of the parameter used to generate the second signal (i.e., a flow rate or pressure within the second instrument 32), the second signal may include a soot concentration or gaseous pollutant component indicating the soot or gaseous pollutant concentration measured by the second instrument 32 and a second instrument time stamp component associated with sampling the exhaust at the first time. The second time stamp component may be generated by a clock associated with the second instrument 32. The second instrument 32 also generates a tertiary signal that includes a second component that is influenced by the flow rate of the first instrument. Like the second signal, the tertiary signal may include the second instrument time stamp component.

The second instrument 32 may be constructed in a variety of different configurations. What is important is that the second instrument 32 measures the second flow rate or pressure within the second instrument 32 and the soot or gaseous pollutant concentration of the exhaust supplied to the second instrument 32 via the tube 39. In one configuration, the second instrument 32 includes a flow rate branch for detecting the second flow rate and a soot concentration branch for detecting a soot concentration. The flow rate branch may include the filter 35 that receives a sample of the exhaust supplied to the second instrument 32. The flow rate branch may also include a critical flow orifice (not shown) located downstream of the filter 35. The flow rate branch may further include the flow meter 37 located adjacent to the critical flow orifice for measuring a flow rate of the sample through the critical flow orifice.

The soot concentration branch is connected to the flow rate branch upstream of the filter 35. The soot concentration branch may include the soot concentration sensor 33 for measuring a concentration of soot in the sample. From these measurements, the second instrument 32 determines the second flow rate (or pressure) and the soot concentration of the exhaust supplied to the second instrument 32.

Advantageously, the soot mass flow rate of the exhaust can be calculated using the exhaust flow rate component of the first signal and the soot concentration component of the second signal. As an example, to calculate a soot mass flow rate, two separate instruments 30, 32 may be used to capture the required data. The first instrument 30 captures the exhaust flow rate and the second instrument 32 captures the soot concentration.

The signals from these instruments 30, 32 must be time aligned in order to process the data together. The second signal carrying the soot concentration, $C_{Soot}(t)$, from the second instrument 32 must be aligned with the first signal carrying the exhaust flow rate, $Q_{Exh}(t')$, from the first instrument 30 in order to calculate the soot mass flow rate, $\dot{M}_{Soot}(t)$. It must represent the concentration at the sampling point at the same point in time as the exhaust flow. More particularly, the soot mass flow rate can be calculated by the following expression:

$$\dot{M}_{Soot}(t) = Q_{Exh}(t') * C_{Soot}(t)$$

In accordance with the expression above, $\dot{M}_{Soot}(t)$ is the soot mass flow rate which may have the units of grams per second (g/sec). $Q_{Exh}(t')$ is the exhaust flow rate which may have the units of cubic meters per minute ($m^3$/min). $C_{Soot}(t)$ is the soot concentration which may have the units of milligrams per cubic meter ($mg/m^3$). The calculation can be carried out once the relationship between t and t' is determined.

As noted, a problem that commonly arises is that the first signal and the second signal are not synchronized in time. That is, the first time stamp component of the first instrument 30 is not aligned with the second time stamp component of the second instrument 32. This can occur where the time clock associated with the first instrument 30 begins counting before or after the time clock associated with the second instrument 32 begins counting. It can also occur where the time clock associated with the first instrument 30 begins counting at a different initial time value than the initial time value used by the time clock associated with the second instrument 32.

If the alignment is off by even a small amount, the integration error becomes quite large when the total soot mass is calculated, as shown by integrating the soot mass flow rate:

$$M_{Soot} = \int \dot{M}_{Soot}(t) dt$$

In the above equation, $M_{Soot}$ is the total Mass of Soot integrated over the entire test. For example, the error is quite large where the time alignment of the signals is off by a few seconds or fractions of seconds in either direction. If the second signal is ahead of the first signal, the soot from a combustion event is measured before the increase in exhaust flow rate. This is not realistic and the calculated soot mass flow rate will be much too low. Conversely, where second signal is behind the first signal, an increase in the soot concentration comes after an increase in the exhaust flow rate. As a result, calculated soot mass flow rate will be much too high.

Still referring to FIG. 1, the system 20 includes a synchronization module 34 that solves the time alignment problem by synchronizing the first signal and the second signal. The synchronization module 34 receives and processes the first signal, the second signal, and the tertiary signal. It should be appreciated that any method or device for communicating the first signal, the second signal, and the tertiary signal from the first instrument 30 and the second instrument 32 to the synchronization module 34 may be used. For example, the synchronization module 34 may be electrically connected to the first instrument 30 and the second instrument 32. In response to receiving the first signal, the second signal, and the tertiary signal, the synchronization module 34 determines a time relationship between the first signal and the second signal. The synchronization module 34 performs this task by comparing the first flow rate component and the first instrument time stamp component of the first signal to the tertiary signal and the second instrument time stamp component of the tertiary signal.

The synchronization module 34 determines a time shift value that separates the first instrument time stamp of the first signal and the second instrument time stamp of the tertiary signal. The synchronization module 34 determines the time relationship between the first signal and the second signal by equating the time relationship between the first signal and the second signal to the time shift value between the first signal and the tertiary signal. This operation can be performed because the first signal and the tertiary signal are comparable, as the first signal indicates the exhaust flow rate measured by the first instrument 30 and the tertiary signal indicates a signal measured by the second instrument 32 that has been influenced by the first signal. Accordingly, the exhaust flow rate component of the first signal influences the filter flow rate or pressure component of the tertiary signal such that the time shift between the first time stamp component and the second time stamp component can be determined.

While the synchronization module 34 is described as determining the time shift between the first time stamp component and the second time stamp component, the synchronization module 34 may additionally or alternatively determine the time shift between the first signal and the second signal by comparing any parameter that is influenced by exhaust flow located within the exhaust path 24. For example, the synchronization module 34 may determine the time shift by using a correlation between a pressure of the exhaust passing by the first instrument 30 and a pressure of the exhaust within the second instrument 32 via the tube 39. The influence of the pressure of the exhaust on a flow rate within the second instrument can be expressed as:

$$Q_f = k \frac{P}{\sqrt{T}}$$

In accordance with the expression above, $Q_f$ is the second flow rate of the exhaust within the second instrument 32. Still referring to the expression above, k is a constant, P is the pressure of the exhaust within the second instrument 32, and T is the temperature of the exhaust within the second instrument 32. As this expression shows, the pressure of the exhaust within the second instrument 32 will fluctuate whenever the second flow rate fluctuates. Accordingly, pressure can also be used to determine the time shift between the first signal and the second signal. As such, the correlation between the pressure of the exhaust and the exhaust flow rate can be used in place of, or to verify, the time shift value that is determined using the tertiary signal.

The synchronization module 34 aligns the first signal with the second signal by subtracting the time shift value from the first instrument time stamp component of the first signal to generate a synchronized first signal having a synchronized exhaust flow rate component. Then the synchronization module 34 calculates a soot mass flow rate by calculating the product of the synchronized exhaust flow rate component of the synchronized first signal and the soot concentration component of the second signal. As such, the first signal and the second signal are time aligned at the first time. In some circumstances, this may be sufficient where the clock associated with the first instrument 30 counts at the same frequency as the clock associated with the second instrument 32. However, often there is a gain or loss between the clock associated with the first instrument 30 and the clock associated with the second instrument 32. Accordingly, the first signal and the second signal may become unsynchronized or drift apart even if the first signal and the second signal are aligned at a first time. The remedy for this problem can be referred to as time dilation.

When long time intervals are recorded it may happen that one of the two instruments 30, 32 may gain or lose time with respect to the other of the two instruments 30, 32. However, for a correct and accurate result, the signals from different instruments 30, 32 that are used together in calculations must be accurately aligned at all points in time. The gain or loss of several seconds over many hours, which might be expected from typical electronic timing devices, can render results from later times in a testing interval invalid.

An advantage of the system 20 and the method disclosed is that this clock rate problem can be overcome. Simply put, the system 20 and method disclosed can match up the signal at the beginning of a testing interval, at the end of the testing interval, and then if a different time shift is observed, can stretch or contract one of the first signal and the second signal time stamps according to the difference in time shifts observed to bring them into alignment at the same time shift over the entire testing interval. By way of example, the testing interval may span several seconds, minutes, hours, or days.

To resolve the different clock rate between the first signal and the second signal, the first instrument 30 measures the exhaust flow rate at different times along a testing interval. In response to measuring the exhaust flow rate at different times, the first instrument 30 generates a first array containing a plurality of data pairs spaced by a first time scale. Each data pair of the first array indicates the exhaust flow rate and corresponding first instrument time stamp.

The second instrument 32 measures the soot concentration at different times along the testing interval to generate a second array containing a plurality of data pairs spaced by a second time scale. Each data pair of the second array indicates the soot concentration and corresponding second instrument time stamp. The second instrument 32 also measures the filter flow rate at different times along the testing interval to generate a tertiary array containing a plurality of data pairs spaced by the second time scale. Each data pair of the tertiary array indicates the filter flow rate and corresponding second instrument time stamp. It should be appreciated that a time dilation between the first signal and the second signal exists where the first time scale is different than the second time scale.

To resolve the time dilation between the first signal and the second signal, the synchronization module 34 determines a time relationship between the first array and the second array by comparing the first array and the second array. In response to comparing the first array and the second array, the synchronization module 34 converts the first array to the second time scale based on the time relationship between the first array and the second array and generates a synchronized first array as a result of this conversion. The synchronization module 34 may then calculate a soot mass flow rate for different times along the testing interval by calculating the product of the synchronized first array and the second array.

As used herein, the term module may be replaced with the term circuit. The term module may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor (shared, dedicated, or group) that executes code; memory (shared, dedicated, or group) that stores code executed by a processor; other suitable hardware components that provide the described functionality; or a combination of some or all of the above, such as in a system-on-chip.

The term code, as used above, may include software, firmware, and/or microcode, and may refer to programs, routines, functions, classes, and/or objects. The term shared processor encompasses a single processor that executes some or all code from multiple modules. The term group processor encompasses a processor that, in combination with additional processors, executes some or all code from one or more modules. The term shared memory encompasses a single memory that stores some or all code from multiple modules. The term group memory encompasses a memory that, in combination with additional memories, stores some or all code from one or more modules. The term memory may be a subset of the term computer-readable medium. The term computer-readable medium does not encompass transitory electrical and electromagnetic signals propagating through a medium, and may therefore be considered tangible and non-transitory. Non-limiting examples of a non-transitory tangible computer readable medium include nonvolatile memory, volatile memory, magnetic storage, and optical storage. The present disclosure also sets forth a method of synchronizing signals of an exhaust sampling system, such as the exhaust sampling system 20 described above.

This method includes first synchronizing the first and second signals overall (i.e., aligning the positions of the first and second signals in time), followed by stretching or compressing the first signal to match the time in the second signal (or vice versa). While stretching or compressing one of the first signal and the second signal is described as being performed following alignment of the first signal and the second signal, it is possible to both align the first signal and the second signal and to stretch or compress one of the first signal and the second signal at the same time.

Figure 2A:
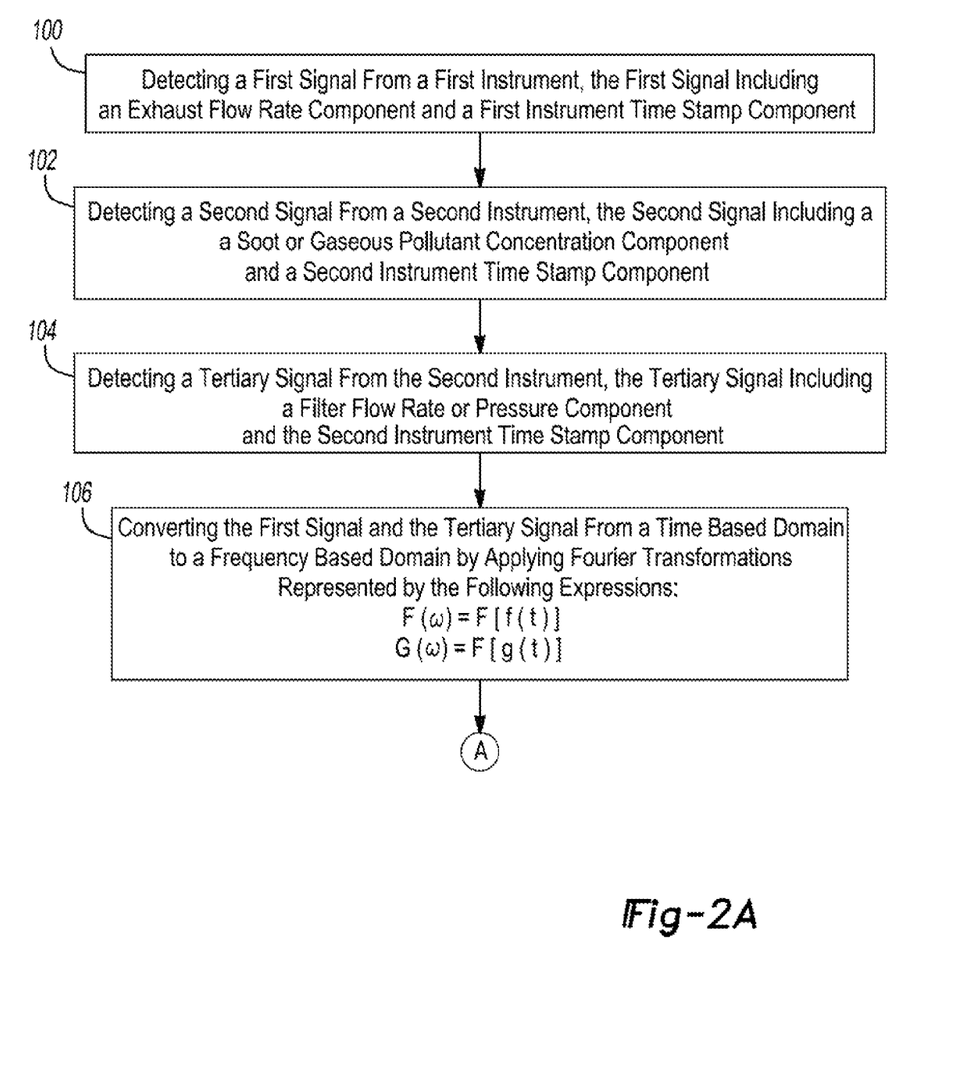
FIG. 2A is a flow diagram illustrating an exemplary method for synchronizing the time alignment of multiple signals in accordance with the subject disclosure.
Figure 2B:
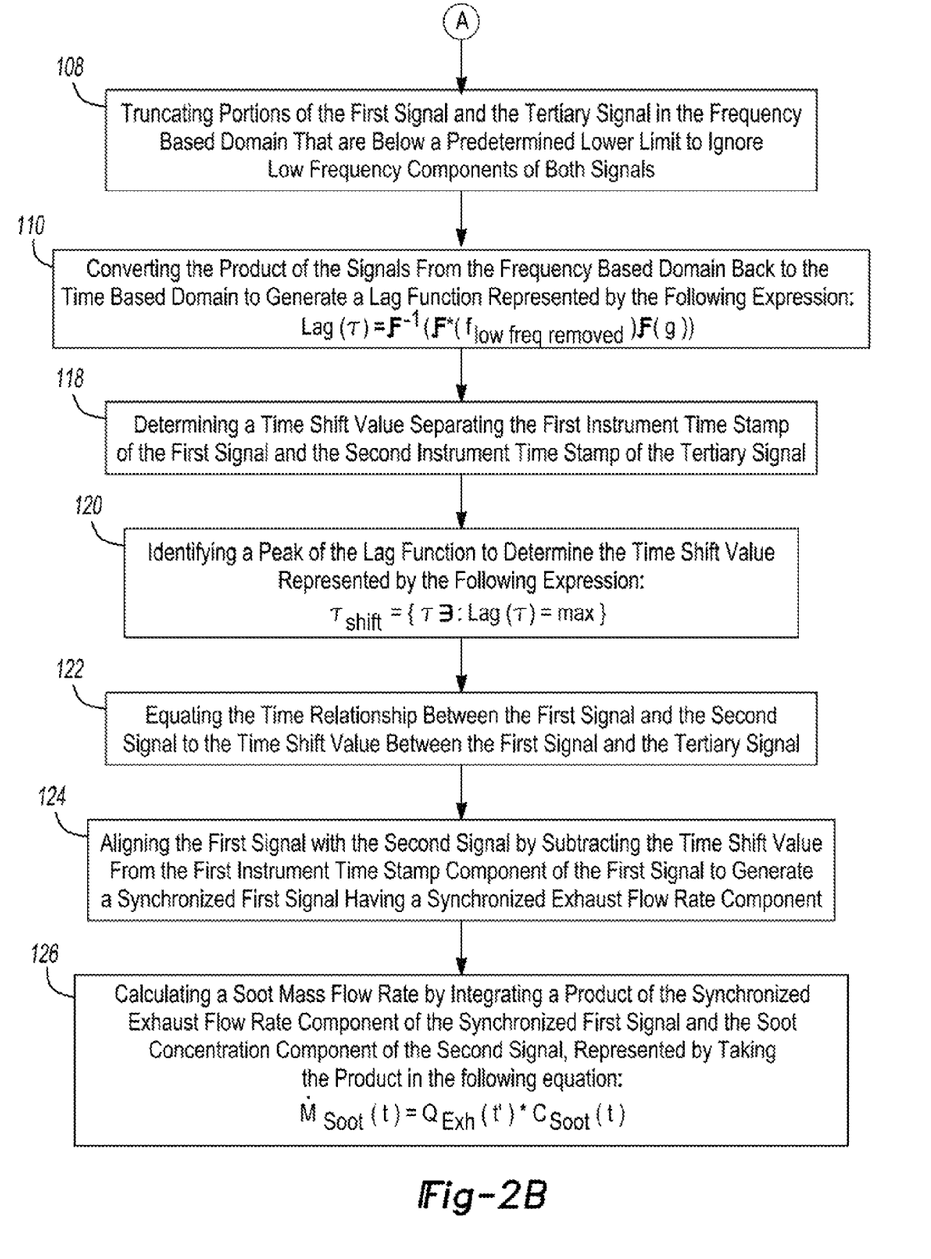
FIG. 2B is a continuation of the flow diagram in FIG. 2A and illustrates the exemplary method for synchronizing the time alignment of multiple signals in accordance with the subject disclosure.

With references to FIGS. 2A and 2B, the method first achieves synchronization by aligning the first signal and the second signal at a first time. The method includes step 100 of detecting a first signal from a first instrument 30. The first signal includes an exhaust flow rate component indicating an exhaust flow rate from an engine 22. The first signal also includes a first instrument time stamp component associated with sampling the exhaust at a first time. The method also provides for step 102 of detecting a second signal from a second instrument 32. The second signal includes a soot or gaseous pollutant concentration component indicating the soot or gaseous pollutant concentration of exhaust within the second instrument 32. The second signal also includes a second instrument time stamp component associated with sampling the exhaust at the first time.

The method also includes step 104 of detecting a tertiary signal from the second instrument 32. The tertiary signal includes a filter flow rate or pressure component indicating the filter flow rate and/or internal pressure, respectively, of the exhaust within the second instrument 32. The tertiary signal also includes the second instrument time stamp component. The method includes several steps of performing mathematical operations. The method will identify a time lag between the first signal and the tertiary signal by integrating a mathematical coincidence function relating the first signal and the tertiary signal. The mathematical coincidence function may be represented by the following expression, which is a function of the time lag ($\tau$):

$$f \ast g(\tau) = \int f(t) g(t-\tau) dt$$

In accordance with the expression above, f is the first signal and g is the tertiary signal. Tau ($\tau$) is the time delay between the first signal and the second signal which may have the units of seconds (sec). The following describes how Tau is determined.

In response to identifying the time lag between the first signal and the tertiary signal, the method includes step 106 of converting the first signal and the tertiary signal from a time based domain to a frequency based domain. This conversion step includes applying Fourier transformations to the first signal and the tertiary signal. The Fourier transformations may be represented by the following expressions:

$$F(\omega) = \mathcal{F}[f(t)]$$

$$G(\omega) = \mathcal{F}[g(t)]$$

In accordance with the expressions above, f(t) is the first signal and g(t) is the tertiary signal, both of which are in the time based domain. F($\omega$) is the first signal in the frequency based domain and G($\omega$) is the tertiary signal in the frequency based domain. $\mathcal{F}$ is used to indicate the Fourier transformation.

The method shown in FIGS. 2A and 2B takes advantage of the filter flow rate (tertiary signal) sharing many high-frequency components with the exhaust flow rate (first signal). This physical characteristic can be seen in other signals as well. For example, and as described above, the tertiary signal could be generated based on the pressure within the second instrument 32, as changes in the pressure of the exhaust flow cause similar and virtually instantaneous pressure changes in the exhaust disposed inside the second instrument 32.

Changes in the ambient air pressure, which change slowly over time, can occur as the first instrument 30 and the second instrument 32 of the system 20 are carried by a vehicle to higher and lower altitudes. Such low-frequency pressure differences are accounted for in step 108 by truncating portions of the first signal and the tertiary signal in the frequency based domain that are below a predetermined lower limit to eliminate the resulting slower variations in ambient air pressure. Variations based on ambient air pressure are observable at low frequencies so step 108 removes this potential error by clipping low frequency portions of the first signal and the tertiary signal when the signals are represented in the frequency based domain. By way of example, the predetermined lower limit can be set to remove frequencies lower than about 0.00610 Hertz (Hz).

After converting the first signal and the tertiary signal to the frequency based domain and removing the low frequencies, the method multiplies the complex conjugate of the first signal and the tertiary signal to generate a product of the signals in the frequency based domain. In response to multiplying the first signal and the tertiary signal, the method includes step 110 of converting the product of the signals from the frequency based domain back to the time based domain to generate a lag function. The inverse Fourier transformation of the product of the signals in the frequency based domain may be represented mathematically by the following expression:

$$\text{Lag}(t) = \mathfrak{F}^{-1}(\mathfrak{F}^*(f_{low\ freq\ removed})\mathfrak{F}(g))$$

In accordance with the expression above, f is the first signal and g is the tertiary signal, both of which are in the time based domain. $\mathsf{F}$ is used to indicate the Fourier transformation, $\mathsf{F}^{-1}$ is used to indicate the inverse Fourier transformation and $\mathsf{F}^*$ indicates the complex conjugate of the Fourier transformation.

The method continues with step 120 of identifying a peak of the lag function to determine the time shift value. There should be a sharp peak where the exhaust flow influences of the two signals are well matched. In other words, the highest or maximum value of the lag function represents the time shift value. Mathematically, the time shift value may be represented by the following expression:

$$\tau_{shift} = \{\tau \ni : \text{Lag}(\tau) = \max\}$$

In accordance with the expression above, Tau ($\tau$) is the time delay between the first signal and the second signal which may have the units of seconds (sec). Tau shift ($\tau_{shift}$) is the time shift between the first signal and the tertiary signal which may have the units of seconds (sec). Lag(t) is the lag function. Finally, max indicates that the time shift is the tau value for which the lag function has a maximum.

The method may alternatively perform step 120 of determining the time shift between the first signal and the second signal by comparing any parameter that correlates to exhaust flow. For example, the synchronization module 34 may determine the time shift by using a correlation between a pressure of the exhaust passing by the first instrument 30 and a pressure within the second instrument 32. The flow of the exhaust within the second instrument can be expressed as:

$$Q_f = k\frac{P}{\sqrt{T}}$$

In accordance with the expression above, $Q_f$ is the second flow rate of the exhaust within the second instrument 32. Still referring to the expression above, k is a constant, P is the pressure of the exhaust within the second instrument 32, and T is the temperature of the exhaust within the second instrument 32. As this expression shows, the second flow rate of the exhaust within the second instrument 32 will fluctuate whenever the internal pressure of the exhaust sample in the instrument fluctuates. Accordingly, pressure can also be used to determine the time shift between the first signal and the second signal. As such, the correlation between the pressure of the exhaust and the exhaust flow rate can be used in place of step 120 or to verify the time shift value that is determined using the tertiary signal in accordance with step 120.

Still referring to FIGS. 2A and 2B, the method includes the step 122 of equating the time relationship between the first signal and the second signal to the time shift value between the first signal and the tertiary signal. This step is appropriate because the first signal and the tertiary signal both include components that are influenced by the flow rate of the exhaust and therefore follow one another. The method includes step 124 of aligning the first signal with the second signal by subtracting the time shift value from the first instrument time stamp component of the first signal to generate a synchronized first signal having a synchronized exhaust flow rate component. If dilation was not required, we could at this point calculate the soot mass flowrate. By generating the synchronized first signal the method may then proceed to step 126 of calculating a soot mass flow rate by calculating the product of the synchronized exhaust flow rate component of the synchronized first signal and the soot concentration component of the second signal. Again, the soot mass flow rate can be calculated by taking the product of the following expression:

$$\dot{M}_{Soot}(t) = Q_{Exh}(t')^* C_{Soot}(t)$$

In accordance with the expression above, $\dot{M}_{Soot}(t)$ is the soot mass flow rate which may have the units of grams per second (g/sec). $Q_{Exh}(t')$ is the exhaust flow rate which may have the units of cubic meters per minute (m$^3$/min). $C_{Soot}(t)$ is the soot concentration which may have the units of milligrams per cubic meter (mg/m$^3$).

Figure 3:
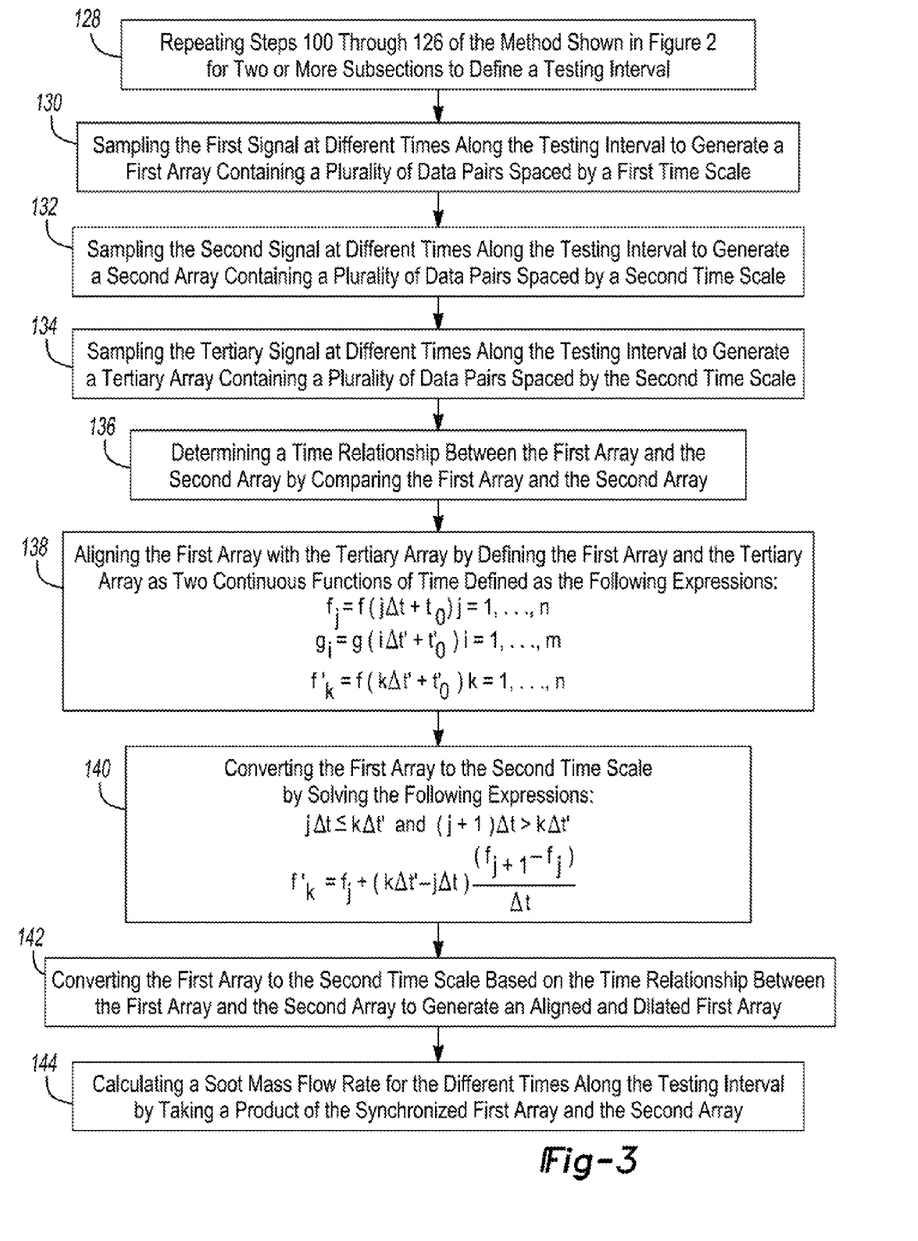
FIG. 3 is a flow diagram illustrating an exemplary method for synchronizing the clock rates of two recorders with a time dilation of multiple signals in accordance with the subject disclosure.

Now referring to FIG. 3, the method achieves synchronization by resolving the clock rates of the first signal with respect to the second signal. Begin by selecting two sections from the start and end of the first and tertiary signals (perhaps the START section would begin at 5% and end at 15% of the total time and the END section would be from 85% to 95%). The method further includes step 128 of repeating steps 100 through 126 of the method for each of these two sections. Note that if required any number of sections could be used, not just one. For example, one of the computer clocks may be non-linear due to slowing over the course of the day because of battery voltage or the effect of temperature on the device. In this case, the present method could be used to break the signal into any number of sections and repeat the method on each section. The following description is based on the simplest case; a single section with two endpoints.

Let Tau$_{start}$ be the time delay between the first and tertiary signals during the START time period. Let Tau$_{end}$ be the time delay between the first and tertiary signals during the END time period. The difference between Tau$_{start}$ and Tau$_{end}$ show the difference between the interval time of the first signal and the tertiary signal. For example, if Tau$_{start}$ and Tau$_{end}$ are the same, then both signals had exactly the same time between samples, the same clock rates. If, on the other hand, Tau$_{end}$−Tau$_{start}$=4 seconds, four (4) more seconds elapsed between the beginning and end of the tertiary signal than that of the first signal.

The foregoing time discrepancy between the first signal and the tertiary signal may be caused by slightly different clock speeds of separate computers used to record the first signal and the tertiary signal. In the preceding example, one of the computer's clock might lose four (4) seconds over the course of an eight (8) hour sampling period relative to the other computer's clock. The following sections describe the details of this process.

The method includes step 130 of sampling the first signal at different times along the testing interval to generate a first array. The first array contains a plurality of data pairs spaced by a first time scale. Each data pair in the first array indicates the exhaust flow rate from the engine 22 and corresponding first instrument time stamp. At step 132, the method includes sampling the second signal at different times along the testing interval to generate a second array. The second array contains a plurality of data pairs spaced by a second time scale that is different than the first time scale. Each data pair in the second array indicates the soot concentration of exhaust passing by the second instrument and corresponding second instrument time stamp.

The method includes at step 134, sampling the tertiary signal at different times along the testing interval to generate a tertiary array. The tertiary array contains a plurality of data pairs spaced by the second time scale. As such, it should be appreciated that the second array and the tertiary array have the same time scale and the first array has a time scale that is different from the time scale of the second array and the tertiary array. Each data pair in the tertiary array indicates the filter flow rate or pressure of exhaust in the second instrument 32 and corresponding second instrument time stamp.

In response to determining the first array, the second array, and the tertiary array, the method proceeds to step 136 of determining a time relationship between the first array and the second array by comparing the first array and the second array. The method again includes several steps of performing mathematical operations. The method includes step 138 of aligning the first array with the tertiary array by defining the first array and the tertiary array as two continuous functions of time. The two continuous functions of time may be defined as the following expressions:

$$f_j = f(j\Delta t + t_0) \, j = 1, \ldots, n$$

$$g_i = g(i\Delta t' + t_0') \, i = 1, \ldots, m$$

$$f'_k = f(k\Delta t' + t_0') \, k = 1, \ldots, n$$

In accordance with the expressions above, f is the first signal and $f_j$ is the $j^{th}$ element of the first array. Delta t ($\Delta t$) is the time units spacing the data pairs of the first array which may have the units of seconds (sec). Still referring to the expressions above, $g_i$ is the tertiary array and Delta t prime ($\Delta t'$) is the time units spacing the data pairs of the tertiary array which may have the units of seconds (sec). $f_k$ is the $k^{th}$ element of the first array after we have applied the time of the tertiary array to the first array.

In response to defining the first array and the tertiary array as two continuous functions of time, the method continues with step 140 of converting the first array to the second time scale by solving the following expressions:

$$j\Delta t \le k\Delta t' \text{ and } (j+1)\Delta t > k\Delta t'$$

$$f'_k = f_j + (k\Delta t' - j\Delta t)\frac{(f_{j+1} - f_j)}{\Delta t}$$

Here is described the method of Linear Interpolation used to calculate the new values of f for the array f'. For each k, choose j such that the first equation is true. In accordance with the expression above, f is the first signal and $f_j$ is the jth element of the first array. Delta t ($\Delta t$) is the time units spacing the data pairs of the first array which may have the units of seconds (sec). Still referring to the expressions above, $f_k$ is the kth element of the first array which now uses the second array's time interval. Delta t prime ($\Delta t'$) is the time units spacing the data pairs of the tertiary array which may have the units of seconds (sec).

The method includes step 142 of converting the first array to the second time scale based on the time relationship between the first array and the second array to generate an aligned and dilated first array. In response to converting the first array to the second time scale, the method proceeds to step 144 of calculating a soot mass flow rate for the different times along the testing interval by taking the product of the synchronized first array (Exhaust Flow) and the second array (Soot Concentration). The total Soot expelled from the tailpipe will be the integral of the Soot Mass Flow Rate over the total sampling time.

The method described herein and shown in FIGS. 2A, 2B, and 3 are presented for the purpose of illustration and disclosure. As evinced by the appended claims, the method is not limited to all of the steps described herein and labeled as reference numerals 100 through 144 in FIGS. 2 and 3. Accordingly, the method may be successfully practiced by performing only some of these steps. Additionally, the method is not limited to the order of the steps disclosed herein and illustrated in FIGS. 2A, 2B, and 3. The method may be practiced by performing these steps in an alternative order or sequence unless expressly specified otherwise in the claims.

The foregoing description of the embodiments has been provided for the purposes of illustration and description. It is not intended to be exhaustive or limiting. Obviously, many modifications and variations of the present disclosure are possible in light of the above teachings and may be practiced otherwise than as specifically described while within the scope of the appended claims. The use of the word "said" in the appended system claims refers to an antecedent that is a positive recitations meant to be included in the coverage of the system claims whereas the word "the" precedes a word not meant to be included in the coverage of the system claims. This convention is inapplicable to the appended method claims.

What is claimed is:

1. A system for sampling exhaust produced by an engine comprising:
    a first instrument measuring a first flow rate of the exhaust leaving the engine and generating a first signal including a first flow rate component indicating said first flow rate and a first instrument time stamp component associated with sampling at a first time;
    a second instrument measuring a pollutant concentration and generating a second signal including a pollutant concentration component indicating said pollutant concentration and a second instrument time stamp component associated with sampling at said first time and generating a tertiary signal including a component indicating a parameter that has been influenced by said first flow rate and including said second instrument time stamp component; and
    a synchronization module receiving and processing said first signal, said second signal, and said tertiary signal to determine a time relationship between said first signal and said second signal by comparing said first flow rate component and said first instrument time stamp component of said first signal to said influenced parameter component and said second instrument time stamp component of said tertiary signal.

2. The system of claim 1, wherein said synchronization module determines a time shift value that separates said first instrument time stamp of said first signal and said second instrument time stamp of said tertiary signal.

3. The system of claim 2, wherein said synchronization module equates said time relationship between said first signal and said second signal to said time shift value between said first signal and said tertiary signal.

4. The system of claim 3, wherein said synchronization module aligns said first signal with said second signal by subtracting said time shift value from said first instrument time stamp component of said first signal to generate a synchronized first signal having a synchronized exhaust flow rate component.

5. The system of claim 4, wherein said synchronization module calculates a pollutant mass flow rate by calculating the product of said synchronized exhaust flow rate component of said synchronized first signal and said pollutant concentration component of said second signal.

6. The system of claim 1, wherein said first instrument measures said first flow rate at different times along a testing interval and generates a first array containing a plurality of data pairs spaced by a first time scale, each data pair of said first array indicating said first flow rate and said first instrument time stamp.

7. The system of claim 6, wherein said second instrument measures said pollutant concentration at different times along said testing interval to generate a second array containing a plurality of data pairs spaced by a second time scale, each data pair of said second array indicating said pollutant concentration and said second instrument time stamp.

8. The system of claim 7, wherein said second instrument measures said tertiary signal at different times along said testing interval to generate a tertiary array containing a plurality of data pairs spaced by said second time scale, each data pair of said tertiary array indicating said influenced parameter and said second instrument time stamp.

9. The system of claim 8, wherein said synchronization module determines a time relationship between said first array and said second array by comparing said first array and said second array, converts said first array to said second time scale based on said time relationship between said first array and said second array to generate a synchronized first array, and calculates a pollutant mass flow rate for said different times along said testing interval by calculating the product of said synchronized first array and said second array.

10. A system for sampling exhaust comprising:
a first instrument measuring a first flow rate of the exhaust passing by said first instrument and generating a first signal including a first flow rate component indicating said first flow rate and a first instrument time stamp component associated with sampling at a first time;
a second instrument measuring a pollutant concentration and generating a second signal including a pollutant concentration component indicating said pollutant concentration and a second instrument time stamp component associated with sampling at said first time and generating a tertiary signal including a component indicating a parameter that has been influenced by said first flow rate and including said second instrument time stamp component; and
a synchronization module receiving and processing said first signal, said second signal, and said tertiary signal to determine a time relationship between said first signal and said second signal by comparing said first flow rate component and said first instrument time stamp component of said first signal to said influenced parameter component and said second instrument time stamp component of said tertiary signal.

11. A method of synchronizing signals of an exhaust sampling system comprising:
detecting a first signal from a first instrument, the first signal including a first flow rate component indicating a first flow rate of exhaust from an engine and a first instrument time stamp component associated with sampling at a first time;
detecting a second signal from a second instrument, the second signal including a pollutant concentration component indicating the pollutant concentration of exhaust within the second instrument and a second instrument time stamp component associated with sampling at the first time;
detecting a tertiary signal from the second instrument, the tertiary signal including a component indicating a parameter having been influenced by said first flow rate and including the second instrument time stamp component; and
determining a time relationship between the first signal and the second signal by comparing the exhaust flow rate component and the first instrument time stamp component of the first signal to the influenced parameter component and the second instrument time stamp component of the tertiary signal.

12. The method of claim 11, further comprising determining a time shift value separating the first instrument time stamp of the first signal and the second instrument time stamp of the tertiary signal.

13. The method of claim 12, further comprising equating the time relationship between the first signal and the second signal to the time shift value between the first signal and the tertiary signal.

14. The method of claim 13, further comprising aligning the first signal with the second signal by subtracting the time shift value from the first instrument time stamp component of the first signal to generate a synchronized first signal having a synchronized exhaust flow rate component.

15. The method of claim 14, further comprising calculating a pollutant mass flow rate by calculating the product of the synchronized exhaust flow rate component of the synchronized first signal and the pollutant concentration component of the second signal.

16. The method of claim 15, further comprising identifying a time lag between the first signal and the tertiary signal by integrating a mathematical coincidence function relating the first signal and the tertiary signal, the mathematical coincidence function being $f°g \equiv \int f(t)g(t-\tau)dt$;
converting the first signal and the tertiary signal from a time based domain to a frequency based domain by applying Fourier transformations to the first signal and the tertiary signal, the Fourier transformations being $F(\omega)=\mathfrak{F}[f(t)]$ and $G(\omega)=\mathfrak{F}[g(t)]$;
multiplying the complex conjugate first signal and the tertiary signal to generate a product of the signals in the frequency based domain;
converting the product of the signals from the frequency based domain to the time based domain to generate a lag function, the lag function being defined as $Lag(t) = \mathfrak{F}^{-1}(\mathfrak{F}^*(f_{low\ freq\ removed})\mathfrak{F}(g))$; and
identifying a peak of the lag function to determine the time shift value, the time shift value equaling $\tau_{shift} = \{\tau \ni : Lag(\tau) = max\}$.

17. The method of claim 16, further comprising truncating portions of the first signal and the tertiary signal in the frequency based domain that are below a predetermined lower limit to eliminate low frequency variability resulting from variations in ambient air pressure.

18. The method of claim 15, further comprising:
repeating the steps of the method set forth in claim 15 at a second time that is spaced a predetermined number of time units from the first time to define a testing interval;
sampling the first signal at different times along the testing interval to generate a first array containing a plurality of data pairs space by a first time scale, each data pair indicating the exhaust flow rate from the engine and the corresponding first instrument time stamp;
sampling the second signal at different times along the testing interval to generate a second array containing a plurality of data pairs spaced by a second time scale, each data pair indicating the soot concentration of exhaust within the second instrument and the corresponding second instrument time stamp;
sampling the tertiary signal at different times along the testing interval to generate a tertiary array containing a plurality of data pairs spaced by the second time scale, each data pair indicating the filter flow rate of exhaust within the second instrument and the corresponding second instrument time stamp;
determining a time relationship between the first array and the second array by comparing the first array and the second array;
converting the first array to the second time scale based on the time relationship between the first array and the second array to generate a synchronized first array; and
calculating a pollutant mass flow rate for the different times along the testing interval by calculating the product of the synchronized first array and the second array.

19. The method of claim 18, further comprising:
aligning the first array with the tertiary array by defining the first array and the tertiary array as two continuous functions of time, the two continuous functions of time being $f_j=f(j\Delta t+t_0)$ $j=1, \ldots, n$ and $f_k=f(k\Delta t'+t_0')$ $k=1, \ldots, m$; and
converting the first array to the second time scale by solving $$f_k = f_j + (k\Delta t' - j\Delta t)\frac{(f_{j+1} - f_j)}{\Delta t}.$$

20. The system of claim 1, wherein said influenced parameter is a second flow rate of exhaust measured by said second instrument.

21. The system of claim 1, wherein said influenced parameter is a pressure measured by said second instrument.

22. The system of claim 10, wherein said influenced parameter is a second flow rate of exhaust measured by said second instrument.

23. The system of claim 10, wherein said influenced parameter is a pressure measured by said second instrument.

24. The method of claim 11, wherein the influenced parameter is a second flow rate of exhaust measured by the second instrument.

25. The method of claim 11, wherein the influenced parameter is a pressure measured by the second instrument.

* * * * *